(12) United States Patent
Kanauchi et al.

(10) Patent No.: US 6,348,221 B1
(45) Date of Patent: *Feb. 19, 2002

(54) SUBSTANCE ORIGINATING IN GERMINATING SEEDS OF GRAMINEOUS PLANT AND CONTAINING PROTEINS AND INSOLUBLE DIETARY FIBERS AND USE THEREOF

(75) Inventors: Osamu Kanauchi; Kazue Agata, both of Gunma (JP)

(73) Assignee: Kirin Beer Kabushiki Kaisha, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/155,857
(22) PCT Filed: Mar. 5, 1997
(86) PCT No.: PCT/JP97/00671
 § 371 Date: Oct. 5, 1998
 § 102(e) Date: Oct. 5, 1998
(87) PCT Pub. No.: WO97/37674
 PCT Pub. Date: Oct. 16, 1997

(30) Foreign Application Priority Data

Apr. 5, 1996 (JP) .............................. 8-083779
Apr. 5, 1996 (JP) .............................. 8-083780

(51) Int. Cl.[7] .................. A61K 35/78; A61K 35/00; A61K 38/00
(52) U.S. Cl. .................. 424/750; 514/2; 514/867; 424/115
(58) Field of Search .............. 424/195.1, 115, 424/439, 750; 426/481–484, 430, 629, 489; 514/2, 867

(56) References Cited

U.S. PATENT DOCUMENTS

| 5,006,337 | A | * | 4/1991 | Motitschke et al. ..... 424/195.1 |
| 5,009,891 | A | * | 4/1991 | Niwa et al. ............... 424/195.1 |
| 5,135,765 | A | * | 8/1992 | Kishi et al. ................. 426/417 |
| 5,156,877 | A | | 10/1992 | Kishi et al. ................. 426/624 |
| 5,489,440 | A | * | 2/1996 | Ndife et al. ................. 424/489 |
| 5,725,901 | A | * | 3/1998 | Fox ............................. 426/549 |
| 5,728,384 | A | * | 3/1998 | Tokuyama ............... 424/195.1 |

FOREIGN PATENT DOCUMENTS

| GB | 1 219 564 | 1/1971 |
| JP | 03123479 | 5/1991 |
| JP | 03244373 | 10/1991 |
| JP | 06292516 | 10/1994 |
| JP | 06293656 | 10/1994 |
| JP | 06298658 | 10/1994 |
| JP | 06298660 | 10/1994 |
| JP | 07041426 | 2/1995 |
| JP | 07157435 | 6/1995 |
| JP | 07278586 | 10/1995 |
| JP | 08092113 | 4/1996 |
| JP | 08119873 | 5/1996 |
| JP | 08157385 | 6/1996 |
| JP | 08336358 | 12/1996 |

OTHER PUBLICATIONS

Goldberg et al. Nutrit. Rev. vol. 54 (1), pp. 36–37 Jan. 1996.*

D. Mason et al., "Chemical composition of palmyrah (Barassus flabelifer) seed shoots–odiyal.", International Journal of Food Sciences and Nutrition, vol. 45, pp. 287–290, 1994, School of Biological and Molecular Sciences, Oxford Brookes University, Gipsy Lane, Headington, Oxford OX3 OBP, UK.

* cited by examiner

Primary Examiner—Christopher R. Tate
(74) Attorney, Agent, or Firm—Foley & Lardner

(57) ABSTRACT

There is provided a substance which was isolated from the germinated seed of a grass family plant and which contains proteins and insoluble dietary fibers. There are also provided a pharmaceutical composition comprising as an active ingredient said substance which was isolated from the germinated seed of a grass family plant and which contains proteins and insoluble dietary fibers, and a food composition comprising said substance which was isolated from the germinated seed of a grass family plant and which contains proteins and insoluble dietary fibers, as well as uses of said substance.

19 Claims, 11 Drawing Sheets

2 – 1
Appearance of stool from Comparative Group 1

2 – 2
Appearance of stool from Experiment Group 1

3-1

Mucosa of the large intestine of Comparative Group 1

3-2

Mucosa of the large intestine of Experiment Group 1

Diarrhea score

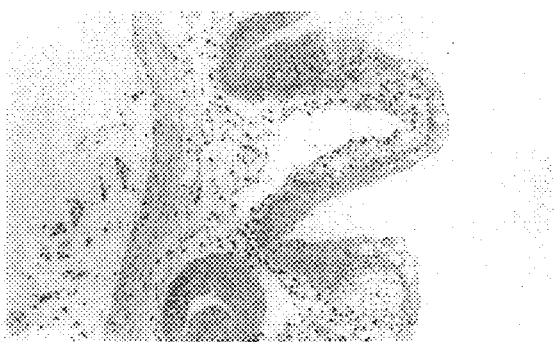
9 - 1 Mucosa of the small intestine of Comparative Group 1a
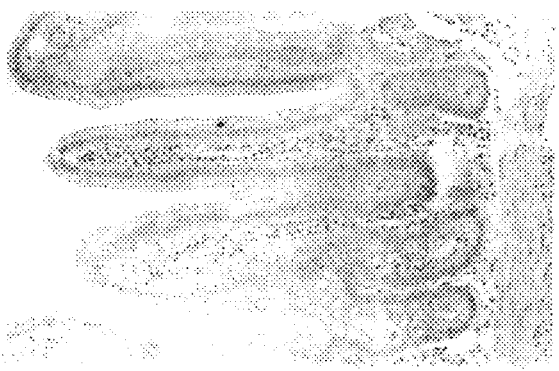
9 - 2 Mucosa of the small intestine of Experiment Group 1a
FIG. 9
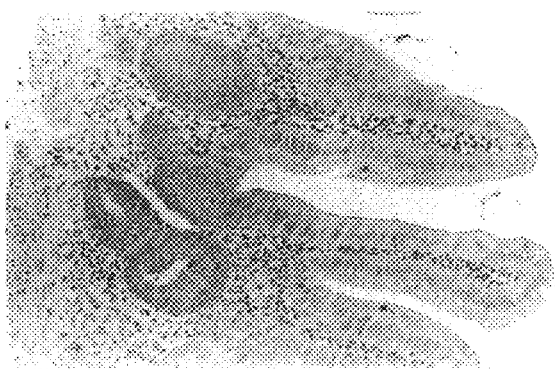
9 - 3 Mucosa of the small intestine of Comparative Group 2a 10-1
Appearance of stool from Comparative Group 1b 10-2
Appearance of stool from Experiment Group 1b 11-1 Peripheral appearance of the anus of Comparative Group 1b 11-2 Peripheral appearance of the anus of Experiment Group 1b

SUBSTANCE ORIGINATING IN GERMINATING SEEDS OF GRAMINEOUS PLANT AND CONTAINING PROTEINS AND INSOLUBLE DIETARY FIBERS AND USE THEREOF

TECHNICAL FIELD

The present invention relates to substances which are isolated from the germinated seed of a grass family plant and which contain proteins and insoluble dietary fibers, and uses thereof.

BACKGROUND ART

Ulcerative colitis has been rapidly growing in the number of patients in Japan since the 1970's. Main complaints of the disease include bloody diarrhea, abdominal pains and the like. It is a chronic and diffuse disease of the large intestine, and, after the initial onset at the rectum, it expands in an ascending manner to the deep part of the large intestine with repeated remissions and flare-ups. The etiology of the disease is unknown at present although its association with the diet has been studied because the incidence of the disease increased with the Westernization of eating habits of the Japanese people. Some researchers suggest that disease may be an autoimmune one, but no proposals on the etiology have obtained public acceptance so far. Very few drugs known today are effective for the treatment of the disease except that a salazosulfapyridine is considered to have a therapeutic effect on mild cases of the disease. However, this drug is an antibiotic which is administered in large quantities and thereby may cause problematic side effects such as diarrhea.

Even a possible therapeutic drug for ulcerative colitis currently under development is a mere improvement of the salazosulfapyridine, and the problem of its side effects has not been completely solved.

Incidentally, cancer ranks top as a cause of deaths in Japan today. It is an extremely intractable disease and the ratio of its successful treatment is not very high at present. Current treatments of cancer include surgical removal, radiation exposure, chemotherapy (administration of anti-cancer agents), immunological therapy, etc., with great strides being made in each method. However, cancer treatment by a single method is believed to be a very difficult challenge.

The surgical process is a very effective means since it removes the tumor cells themselves but its sole use cannot attain a complete cure and, hence, radiation therapy and chemotherapy are simultaneously applied in most cases. The biggest problem encountered in this case is the side effects resulting from the radiation therapy and the chemotherapy. Either therapy attacks cancerous cells having high proliferating activities, so naturally severe damages are also inflicted upon tissues having high rate of growth such as mucosal epithelial cells. As a result, the intestinal mucosa is greatly damaged thereby causing a significant reduction in the absorption of orally administered nutrients and an ensuing severe diarrhea, which ultimately put the patient in a greatly damaged condition. In an extreme case, the patient may eventually die. However, very few effective means have so far been available that can protect the damage of intestinal mucosa and prevent diarrhea.

If the bowels of patients suffering from colon cancer, Crohn's disease, etc., are extensively excised, post-operative dyspepsia and insufficient absorption of electrolytes may cause the patients to have difficulty in normal bowel movement resulting in an extremely high incidence of diarrhea etc., and this can badly affect the patients in leading their normal social life. The same problem is shared by patients who were forced to have an artificial anus for some reason. As a means to solve these problems, there may be mentioned an oral liquid diet that leaves very little residue after absorption. However, the oral liquid diet causes many problems on the part of patients, such as economic burdens, some pains encountered in uptake, and mental burdens due to regulated diets. Thus, there has been a great demand for an effective means that can alleviate these burdens.

Thus, it is an object of the present invention to provide safe materials that can solve the problems stated above.

It is another object of the present invention to provide pharmaceutical compositions and food compositions comprising said material.

It is a further object of the present invention to provide a method of treating ulcerative colitis.

It is a still further object of the present invention to provide a method of preventing or reducing the side effects of cancer treatments.

It is yet another object of the present invention to provide a method of improving the bowel movement of patients who have undergone intestinal ablation or patients with an artificial anus.

DISCLOSURE OF THE INVENTION

After the intensive research conducted to solve the above-mentioned problems, the inventors have discovered that a substance which was separated from the germinated seed of a grass family plant and which contains proteins and insoluble dietary fibers (hereinafter referred to as "the substance containing protein and insoluble dietary fibers") can attain the above objects and thereby have completed the present invention. The gist of the present invention is as follows:

(1) a substance which was isolated from the germinated seed of a grass family plant and which contains proteins and insoluble dietary fibers;

(2) a pharmaceutical composition comprising as an active ingredient a substance which was isolated from the germinated seed of a grass family plant and which contains proteins and insoluble dietary fibers;

(3) a food composition comprising a substance which was isolated from the germinated seed of a grass family plant and which contains proteins and insoluble dietary fibers;

(4) a method of treating ulcerative colitis comprising administering to a patient with ulcerative colitis an effective amount of a substance which was isolated from the germinated seed of a grass family plant and which contains proteins and insoluble dietary fibers;

(5) a method of preventing or reducing the side effects of cancer treatments comprising administering to a patient with a cancer an effective amount of a substance which was isolated from the germinated seed of a grass family plant and which contains proteins and insoluble dietary fibers;

(6) a method of improving the bowel movement of a patient who has undergone intestinal ablation comprising allowing the patient to take an effective amount of a substance which was isolated from the germinated seed of a grass family plant and which contains proteins and insoluble dietary fibers;

(7) a method of improving the bowel movement of a patient with an artificial anus comprising allowing the patient to take an effective amount of a substance which was isolated from the germinated seed of a grass family plant and which contains proteins and insoluble dietary fibers;

(8) use as a pharmaceutical drug of a substance which was isolated from the germinated seed of a grass family plant and which contains proteins and insoluble dietary fibers;

(9) use, for the treatment of ulcerative colitis, of a substance which was isolated from the germinated seed of a grass family plant and which contains proteins and insoluble dietary fibers;

(10) use, for preventing or reducing the side effects of cancer treatments, of a substance which was isolated from the germinated seed of a grass family plant and which contains proteins and insoluble dietary fibers;

(11) use as food of a substance which was isolated from the germinated seed of a grass family plant and which contains proteins and insoluble dietary fibers;

(12) use, for improving the bowel movement of a patient who has undergone intestinal ablation, of a substance which was isolated from the germinated seed of a grass family plant and which contains proteins and insoluble dietary fibers; and

(13) use, for improving the bowel movement of a patient with an artificial anus, of a substance which was isolated from the germinated seed of a grass family plant and which contains proteins and insoluble dietary fibers.

BRIEF EXPLANATION OF THE DRAWINGS

FIG. 8 shows the dry weights of stools from Experiment Group 1a and Comparative Groups 1a and 2a.

FIG. 9 is a set of photographs showing the biological morphology of the appearance of mucosas of the small intestines of Experiment Groups 1a and Comparative Groups 1a and 2a (9-2, 9-1, and 9-3, respectively).

BEST MODE FOR CARRYING OUT THE INVENTION

Figure 1:
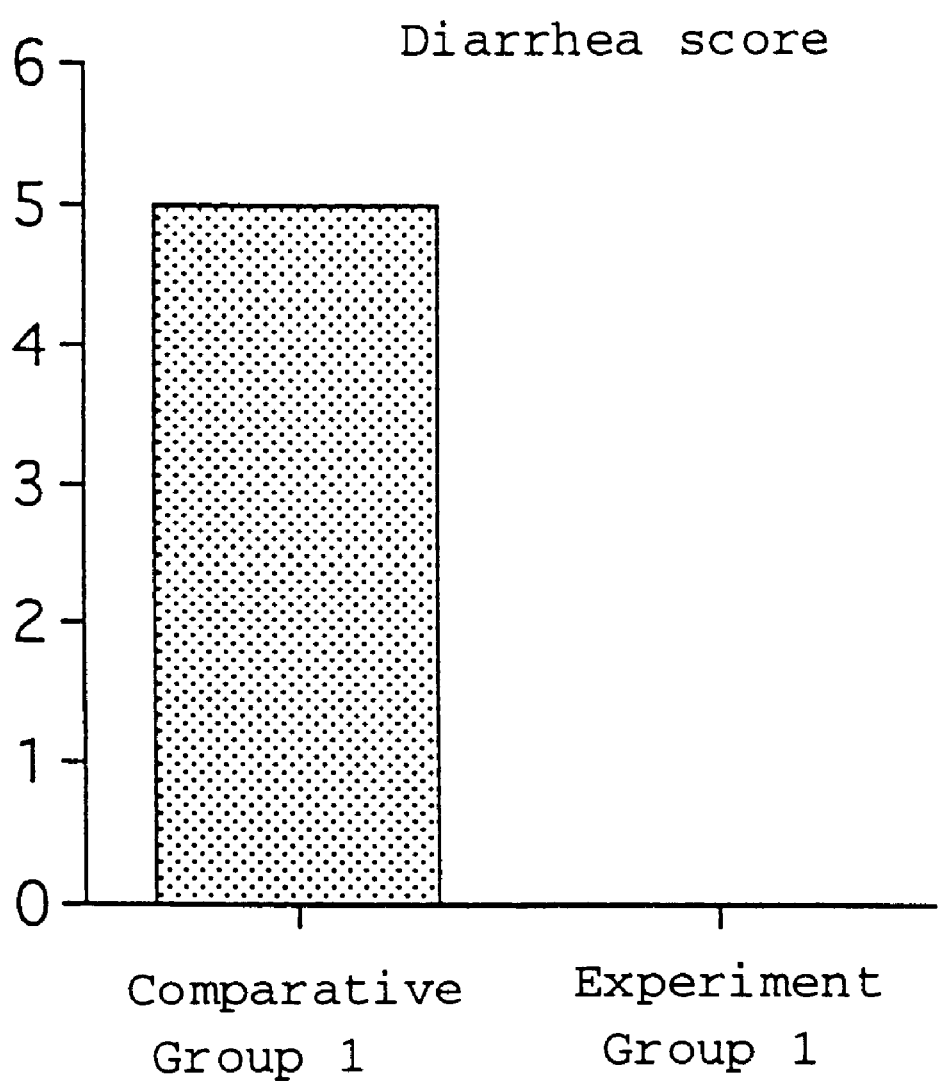
FIG. 1 shows the diarrhea scores of Experiment Group 1 and Comparative Group 1.

As already mentioned, the substance containing proteins and insoluble dietary fibers as used herein is a component obtained from the germinated seed of a grass family plant. Grass family plants refer to all the plants that are classified into the grass family. Specifically, they include, but are not limited to, rice, barley, wheat, rye, millet, barnyard grass, corn, and the like. Among them, rice, barley, and rye are preferred. The germinated seed of a grass family plant may be used as a raw material in separating a substance containing proteins and insoluble dietary fibers with the protein content being 10 to 70% by weight and the insoluble dietary fiber content 20 to 70% by weight, and preferably with the protein content being 10 to 60% by weight and the insoluble dietary fiber content 20 to 50% by weight. To determine the protein content as used herein, then multiplied the nitrogen content is first obtained using the Kjeldahl method and by 6.25 which is a protein conversion coefficient. The content of dietary fibers is the sum of the amounts of all dietary fibers present that are determined based on the method shown in "Dietary Fiber", Innami and Kiriyama, eds., pp. 38–40, 1989, Daiichi Shuppan.

Specific methods for producing such the substance containing proteins and insoluble dietary fibers include the following. i.e, the husks of germinated seeds of a grass family are gradually scraped off (until the weight becomes about 90% that of the original raw material), and then the fractions containing the aleurone layer and the germ are gradually scraped off until the residue is endosperm only (until the weight becomes about 80% that of the original raw material), and the aleurone layer-germ fraction is obtained. The weights mentioned above are just guide figures and the fractionation is preferably carried out with the aleurone layer etc. are examined under an electron microscope.

Economically, it is preferred to use brewer's grains, which are the barley malt remaining after use as the raw material of beer. As a specific example of the method for obtaining the substance containing proteins and insoluble dietary fibers from brewer's grains, the one described in Japanese Post-Unexamined Patent Publication (Kokoku) No. 4-31666 can be used. Thus, the brewer's grains in the wet state are treated by pressing and milling and the pressed and milled product thus obtained may be sieved in the presence of water. The fraction that has passed through the sieve is the substance containing proteins and insoluble dietary fibers. More particularly, brewer's grains in the wet state are first treated by pressing and milling. Although any pulverizer can be used that has a structure capable of exerting a compressive force on the raw material to be treated for pressing and milling of the brewer's grains, a roll mill is specifically preferred. The gap between the rolls is 0.05 to 2 mm, preferably 0.1 to 0.3 mm. When the brewer's grains are to be pressed and milled, a water content in the brewer's grains is preferably adjusted to 65% or higher. Then the pressed and milled product is sieved in the presence of water. In this sieving, the husk remains on the sieve and the substance containing proteins and insoluble dietary fibers passes through it. The size of the openings in the sieve is 5 to 50 mesh, preferably 20 to 50 mesh. In order to obtain efficiently the fraction containing proteins and insoluble dietary fibers, the above-mentioned pressing and milling and sieving operations are preferably repeated 2 to 5 times. The fractions thus obtained as the undersizes through the sieve are usually dried before use. The drying methods include, but are not limited to, drying with warm air at a temperature of 50 to 100° C., and lyophilization. In some cases, the fractions may be used in the wet state, where their water content is preferably adjusted to about 10 to 90%.

The dispersibility of the material into water may be enhanced by converting the contained proteins into smaller molecules using an enzyme, etc. For example, the substance containing proteins and insoluble dietary fibers is dispersed in water of pH 9, which is then subjected to a thermal dispersing treatment such as autoclaving. After the temperature of the dispersion has risen to 50° C., alkali protease (such as Alkalase by Novo) is added to about 0.02% followed by incubation for about 24 hours, where upon the proteins are converted to smaller molecules with an average peptide chain length of about 5 to 8. The average peptide chain length can be determined by the TNBS method (Nakamura et al., Nippon Shokuhin Kogyo Gakkaishi 38: 377–383, 1991).

Furthermore, the content of the insoluble dietary fibers may be enhanced by removing some of the protein fraction. In one method, for example, the substance containing proteins and insoluble dietary fibers is treated by artificial digestion (Matoba et al., Journal of Japanese Society of Food and Nutrition, 34: 415–421, 1981). In the method, the fraction of proteins and insoluble dietary fibers is sequentially reacted in a pepsin-hydrochloric acid solution and then in a pancreatin-hydrochloric acid solution in order to yield an undigested fraction. By this treatment, the content of dietary fibers can be enhanced to as high as 70% by weight. However, this is not the sole examples of the methods that can be applied.

Oral administration of the substance containing proteins and insoluble dietary fibers can not only alleviate severe diarrhea derived from ulcerative colitis, but daily intake of the substance can increase resistance to ulcerative colitis itself. For this purpose, the substance containing proteins and insoluble dietary fibers is preferally taken in at least 1 g, more preferably at least 12 g, per day. Since the substance containing proteins and insoluble dietary fibers is derived from the germinated seed of a grass family plant, it will do no harm even if it is taken excessively and, hence, it can be adopted in daily eating programs. The administration or intake of the substance may be timed before, between, or after meals.

The substance containing proteins and insoluble dietary fibers may be used to prevent or reduce the side effects of cancer treatments. The methods of cancer treatment include the radiation therapy in which a radiation such as gamma rays are applied, the chemotherapy in which anti-cancer drugs such as methotrexate and fluorouracil are administered, and combinations of these methods.

The side effects of cancer treatments include damages to intestinal mucosa and the resultant diarrhea. In accordance with the present invention, the substance containing proteins and insoluble dietary fibers may be given at least one day, preferably one week, before cancer treatment. Alternatively, the substance containing proteins and insoluble dietary fibers may be given concomitantly with or after cancer treatment. The daily dosage for adults is 1 g or more, preferably 12 g or more. The substance is derived from the germinated seed of a grass family plant, so it will do no harm even if it is taken excessively. Accordingly, it is preferably administered continuously during the cancer treatment.

Oral intake of the substance containing proteins and insoluble dietary fibers can promote improvement in the bowel movement of a patient who has undergone massive ablation of the bowels or a patient who wears an artificial anus. For this purpose, the proteins and insoluble dietary fibers are preferably taken in at least 4 g, more preferably at least 12 g, per day, Since the proteins and insoluble dietary fibers are components derived from the germinated seed of a grass family plant, it will do no harm even if it is taken excessively.

The substance containing proteins and insoluble dietary fibers according to the present invention may be added to foods and beverages. Examples of the foods and beverages to which the substance containing proteins and insoluble dietary fibers according to the present invention can be added include those containing natural products or processed products as the derivatives. The substance can be added in an amount of 0.01 to 1 g per gram of food or beverage. The substance containing proteins and insoluble dietary fibers according to the present invention can be added to foods and beverages in various dosage forms such as solutions, suspensions, powders, granules, capsules, and the like.

The substance containing proteins and insoluble dietary fibers according to the present invention which can be formulated as a pharmaceutical preparation. In this case, the mode of drug administration is in no way but exemplary routes of administration may be peroral, enteral and the like. In the case of oral or enteral administration, the substance containing proteins and insoluble dietary fibers can be administered as it is or alternatively it can be administered in the form of a solution, a suspension, powder, granule, a tablet, a capsule, and the like in combination with a pharmaceutically acceptable excipient. In this case, the preparation contains the above substance containing proteins and insoluble dietary fibers according to the present invention in a suitable amount of 1 to 50%, preferably 1 to 30%. Examples of the excipient include: sugars such as lactose, sucrose and glucose; starch, inorganic substances such as calcium carbonate and calcium sulfate; and other commonly used substances such as crystalline cellulose, distilled water, purified water, sesame oil, soybean oil, corn oil, olive oil, and cotton seed oil. In formulating pharmaceutical preparations, additives such as binders, lubricants, dispersants, suspending agents, emulsifiers, diluents, buffers, anti-oxidants, anti-bacterial agents can be used. Other pharmaceutical preparations may be mixed or used in combination. The above preparations may be sterilized.

The present invention is now explained in further detail with reference to the following examples. It should be noted, however, that the scope of the present invention is not limited by these examples in any way. Unless otherwise specified, % means present by weight in the examples.

FORMULATION EXAMPLE 1

Brewer's grains in the wet state (water content: 77.6% by weight) were pressed and milled (the rotating speed of the roller: 100 rpm, the gap between rolls: 0.1 mm), and then screened using a 50 mesh sieve. The fraction that passed through the sieve was dried using a steam dryer and then crushed to give a substance containing proteins and insoluble dietary fibers. The analytical values of the substance were as shown in Table 1 and 2.

Crude protein as shown in Table 1 was determined using Kjeldahl method (the coefficient of nitrogen conversion to protein was set at 6.25), crude fat was determined using the soxhlet extraction method with diethyl ether as the extraction solvent, the ash content was determined by the direct incineration method with the sample placed in a crucible, and the dietary fiber content was determined by calculating the sum of the amounts of hemicellulose, cellulose, and lignin shown in Table 2.

The analyses of hemicellulose, cellulose, and lignin shown in Table 2 were carried out based on the method described in "Dietary Fiber," Innami and Kiriyama eds., pp. 38–40, 1989, Daiichi Shuppan.

TABLE 1

Table of Ingredients

| | (% by weight) |
|---|---|
| Crude protein | 53.4 |
| Crude fat | 12.6 |
| Ash content | 2.0 |
| Dietary fiber | 32.1 |

TABLE 2

Composition of Dietary fiber

| | (%) |
|---|---|
| Hemicellulose | 50.0 |
| Cellulose | 24.0 |
| Lignin | 26.0 |

FORMULATION EXAMPLE 2

With the gap between rolls adjusted to 2 mm, a different kind of brewer's grains was treated as in Formulation Example 1 to give the substance containing proteins and insoluble dietary fibers which was derived from the brewer's grains and which contained different amounts of proteins and insoluble dietary fibers. The analytical values of the substance are shown in Table 3.

TABLE 3

Composition of the substance containing proteins and insoluble dietary fibers as obtained in Formulation Example 3

| Ingredients | (% by weight) |
|---|---|
| Crude protein | 56.1 |
| Crude fat | 12.0 |
| Ash content | 2.8 |
| Dietary fiber | 28.9 |

FORMULATION EXAMPLES 3 AND 4

Using the same method as shown in Formulation Example 2 except that a different kind of brewer's grains was used as the raw material and that the conditions of the roll mill and screening in water were modified, the substance containing proteins and insoluble dietary fibers was obtained which was derived from the brewer's grains and which contained different amounts of proteins and insoluble dietary fibers. The analytical values of the substance are shown in Table 4.

TABLE 4

Composition of proteins and insoluble dietary fibers of Formulation Examples 3 and 4 (% by weight)

| Ingredients | Formulation Example 3 | Formulation Example 4 |
|---|---|---|
| Crude protein | 34.9 | 60.0 |
| Crude fat | 12.0 | 12.0 |
| Ash content | 3.0 | 2.8 |
| Dietary fiber | 50.1 | 25.0 |

FORMULATION EXAMPLE 5

Starting with the substance containing proteins and insoluble dietary fibers which obtained in Formulation Example 1, a material having good dispersibility in water was prepared.

Fifty grams (in the dry state) of the substance containing proteins and insoluble dietary fibers as obtained in Formulation Example 1 was weighed, adjusted to pH 9 with sodium hydroxide and further adjusted to make 1 liter. The mixture was subjected to a heat treatment such as autoclaving (121° C., 10 min) and then cooled to 50° C. Thereafter, about 0.02% of alkaline protease (such as Alkalase by Novo) followed by incubation for 24 hours.

Subsequently, thermal-denaturing of the enzyme and lyophilization were conducted. The lyophilized product was crushed to yield a substance having good dispersibility in water.

The average peptide chain length of the substance was determined by the TNBS method (Nakamura et al., Nippon Shokuhin Kogyo Gakkaishi 38: 377–383, 1991) and found to be about 5 to 8.

FORMULATION EXAMPLE 6

A material with an enhanced content of dietary fibers was prepared from the substance containing proteins and insoluble dietary fibers that had been obtained in Formulation Example 1.

One hundred grams of the fraction obtained in Formulation Example 1 was taken as a sample; 1600 ml of an enzyme solution (0.087% pepcin/0.096 N HCl+0.03 M NaCl) and, furthermore, 1200 ml of 0.1 M NaHCO3 were added. The mixture was thermally denatured by incubating at 37° C. f or 4 hours. washing with water was performed until a neutral filtrate came out; thereafter, 1000 ml of an enzyme solution (2.17% pancreatin/Tris-HCl 0.5 M, pH8) and, furthermore, 4000 ml of 0.01 N HCl were added. The mixture was thermally denatured by incubating at 37° C. for 24 hours or longer (26 hours in this case); it was then washed, filtered, lyophilized and crushed. By these treatments, the protein content became 15% and the dietary fiber content 70%.

TEST EXAMPLE 1

The substance containing proteins and insoluble dietary fibers that was prepared in Formulation example 1 was tested to determine whether it could treat the severe diarrhea from ulcerative colitis or abnormalities in the mucosa of colon.

Materials and Methods

As the test animal, male SD rats (3-week old, about 50 g) that had been acclimated to the experimental condition by a preparatory breeding with the solid feed (CE-2, Nippon clea) for one week were used in groups of five animals each. The feeds used in Test Example 1 were as shown in Table 5.

Ulcerative colitis was experimentally developed by giving the animal the feed mixed with dextran sodium sulfate. This is a modification of Iwanaga's method (Journal of Gastroenterology 29: 430–438, 1994). The substance containing proteins and insoluble dietary fibers was also given ad libitum in a mixture with the feed. After breeding for 5 days, the appearances of the stool and the anus were examined and the state of diarrhea was evaluated by scoring. Then the colon was excised and fixed in 10% formalin buffer to prepare sections of the mucosa, and the microscopic view of the mucosa were also examined.

Table 5 Composition of the feed

The basic feed was prepared so as to contain 10% of protein from casein, 5% of lipid from corn oil, 1% of vitamin, 3.5% of minerals, and 0.2% of choline chloride. The weight was adjusted using corn starch.

Comparative Group 1

The basic feed was supplemented with casein and cellulose to provide the protein and dietary fiber contents that would be given by adding 10% of the substance containing proteins and insoluble dietary fibers according to Formulation Example 1. Then, dextran sodium sulfate was added at 4% to induce ulcerative colitis. Experiment Group 1: After the substance containing proteins and insoluble dietary fibers according to Formulation Example 1 was added to the basic feed at 10%, dextran sulfate sodium was added at 4% to induce ulcerative colitis.

|  | Comparative Group 1 | Experiment Group 1 |
|---|---|---|
|  | (% by weight) | |
| Casein | 14.6 | 10 |
| Mineral mix[*1] | 3.5 | 3.5 |
| Vitamin mix[*2] | 1 | 1 |
| Starch | 68.7 | 66.3 |
| Corn oil | 5 | 5 |
| Cellulose | 3 | |
| The substance containing proteins and insoluble dietary fibers according to Formulation example 1 | | 10 |
| Dextran sodium sulfate | 4 | 4 |
| Choline chloride | 0.2 | 0.2 |

[*1]in conformity with AIN-93
[*2]in conformity with AIN-93

Results

Figure 2:
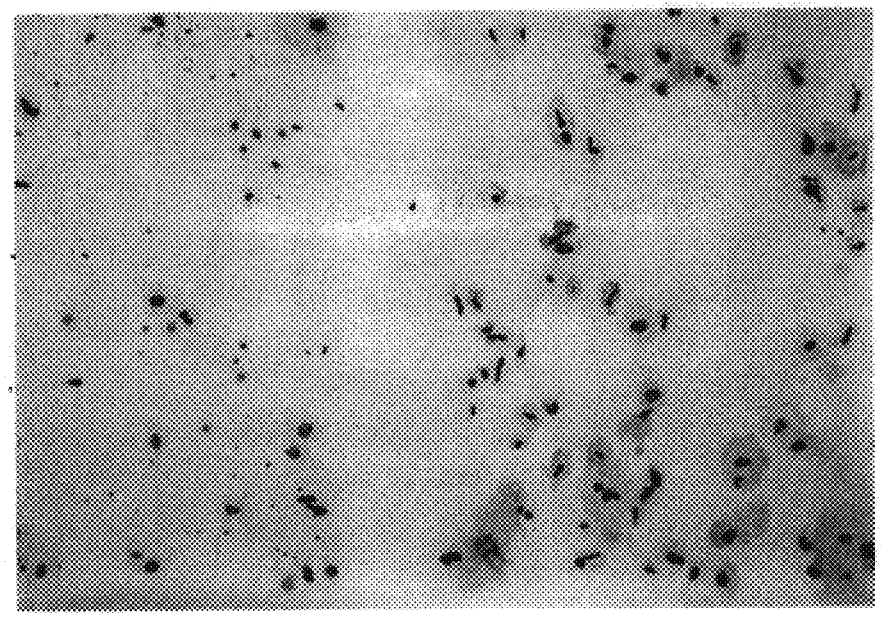
FIG. 2 is a pair of photographs showing the biological morphology of the appearance of stools from Comparative Group 1 (2-1) and Experiment Group 1 (2-1).
Figure 2:
Figure 3:
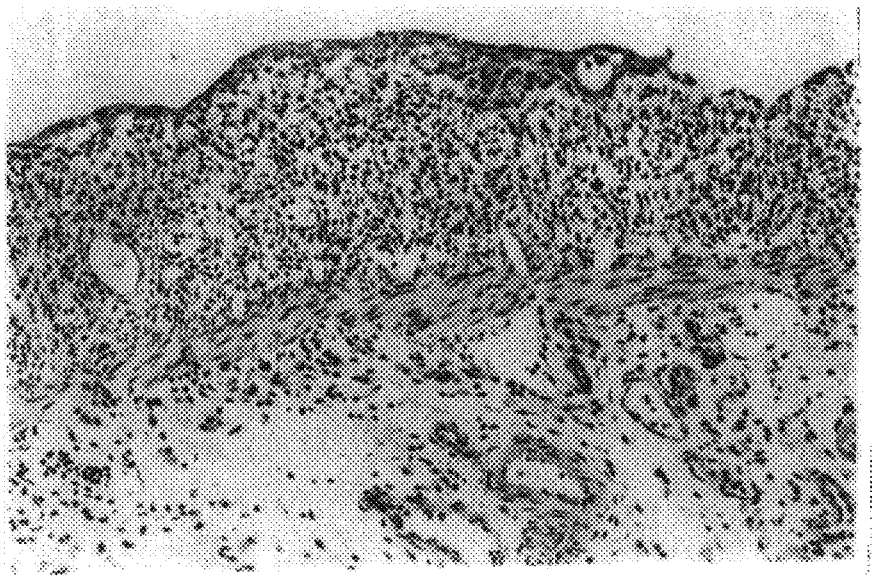
FIG. 3 is a pair of photographs showing the biological morphology of the appearance of the colon mucosas of Comparative Group 1 and Experiment Group 1.
Figure 3:
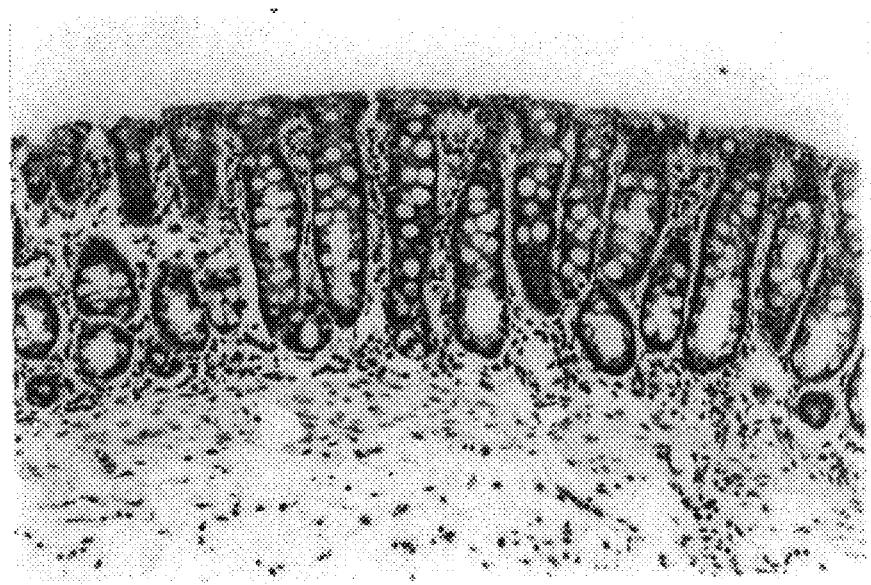

The results are shown in FIG. 1 through 3. FIG. 1 shows the diarrhea scores of Experiment Group 1 and Comparative Group 1. The diarrhea score of FIG. 1 is the average of scores assigned to the rats in each group on the basis of the following 6-level rating: 0, normal; 1, slightly soft; 2, considerably soft; 3, stools cannot be picked up; 4, diarrhea+slightly eroded anus; 5, diarrhea+badly eroded anus. FIG. 2 shows the appearance of stools from Comparative Group 1 (2-1) and Experiment Group 1 (2-1) FIG. 3 shows the appearance of the colon mucosas of Experiment Group 1 and Comparative Group 1. As shown in FIG. 1 through 3, amelioration in diarrhea and prevention of damages in the colon mucosa were observed only when the substance containing proteins and insoluble dietary fibers was taken in. Similarly, diffusion of anus was also prevented only when the substance containing proteins and insoluble dietary fibers was taken in. In both of FIG. 2 and FIG. 3, only one case is illustrated for each experiment group, but normal images of the mucosa were observed in 4 out of 5 animals in the group that took the substance containing proteins and insoluble dietary fibers. As can be seen from this example, the substance containing proteins and insoluble dietary fibers effectively promotes amelioration of symptoms.

Similar results have been obtained for the substance containing proteins and insoluble dietary fibers according to the Formulation Examples 2 through 4.

TEST EXAMPLE 2

The substance containing proteins and insoluble dietary fibers prepared in Formulation Example 1 was tested to determine whether it could treat severe diarrhea associated with ulcerative colitis or abnormalities in the mucosa of colon.

Materials and Methods

These were basically the same as in Test Example 1, but ulcerative colitis was developed by 5-day breeding of all rats with the feed of Comparative Group 1 (the control group) described in Test Example 1; then, the rats were bred for 3 days, with the feed containing no dextran sodium sulfate as shown in Table 6 and the degree of recovery from diarrhea was evaluated by scoring in a similar manner to Test Example 1. From the results of Test Example 1, it was concluded that in the cases of complete recovery from diarrhea, the mucosa of the colon was very close to the normal state.

Table 6 Composition of the Feed

The method of preparing the basic feed was the same as in Test Example 1.

Comparative Group 2

The basic feed was supplemented with casein and cellulose to provide the protein and dietary fiber contents that would be given by adding 10% of the substance containing proteins and insoluble dietary fibers according to Formulation Example 1.

Experiment Group 2

The substance containing proteins and insoluble dietary fibers according Formulation Example 1 was added to the basic feed at 10%.

Experiment Group 3

Salazosulfapyridine (salazopyrine: manufactured by Green Cross K.K.) was added to the feed of Comparative Group 2 at 0.5 g/kg feed (so that the approximate dose would be equal to 50 mg/kg body weight). The dose of salazosulfapyridine was decided by referring to Folia. Pharmacol. Jpn. 102: 343–350 (1993).

|  | Comparative Group 2 | Experiment Group 2 | Experiment Group 3 |
|---|---|---|---|
|  | (% by weight) | | |
| Casein | 14.6 | 10 | 14.6 |
| Mineral mix[*1] | 3.5 | 3.5 | 3.5 |
| Vitamin mix[*2] | 1 | 1 | 1 |
| Starch | 72.7 | 70.3 | 72.65 |
| Corn oil | 5 | 5 | 5 |
| Cellulose | 3 | | 3 |
| The substance containing proteins and insoluble dietary fibers according to Formulation Example 1 | | 10 | |
| Salazopyrine | | | 0.05 |
| Choline chloride | 0.2 | 0.2 | 0.2 |

[*1]in conformity with AIN-93
[*2]in conformity with AIN-93

Results

Figure 4:
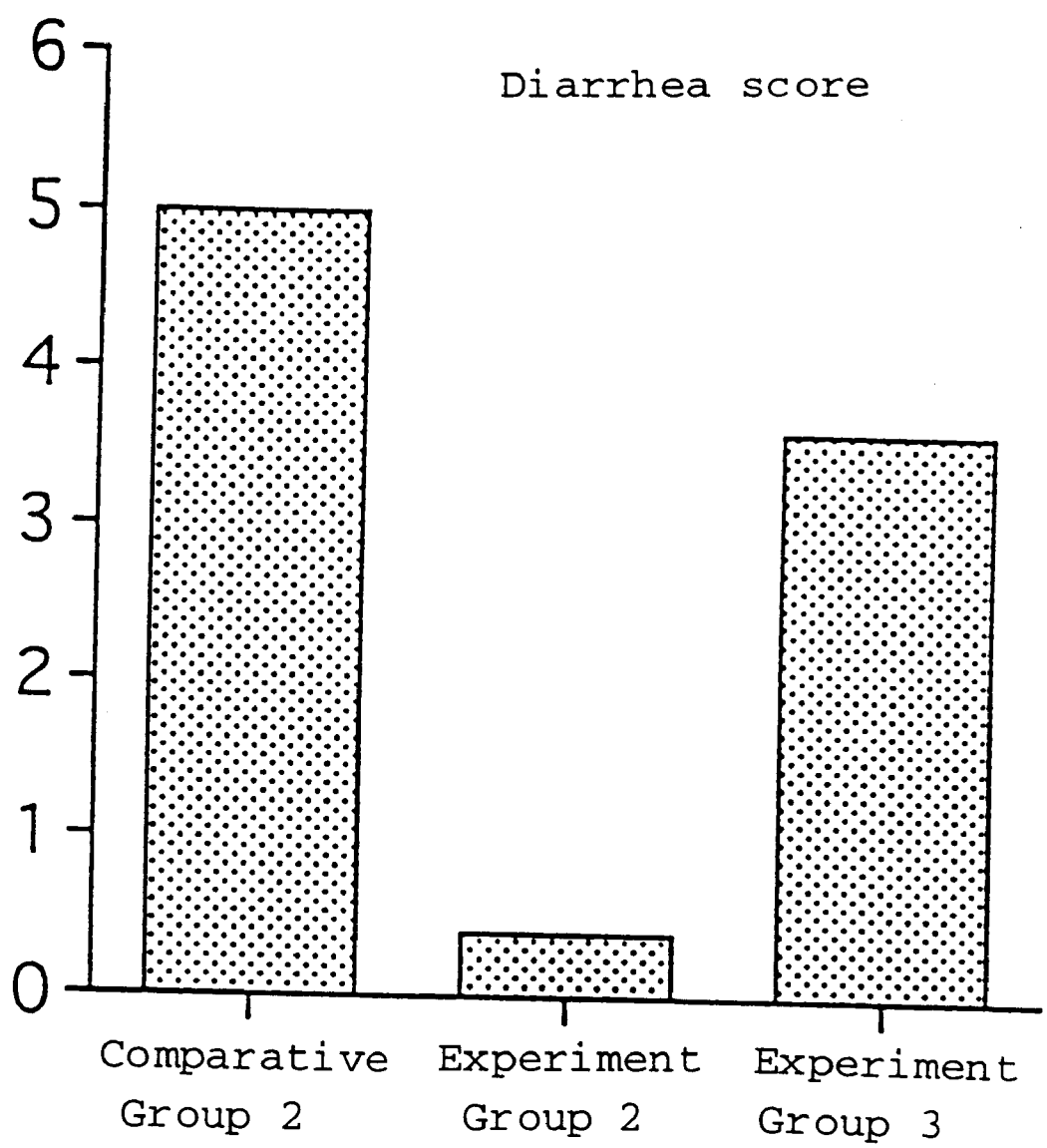
FIG. 4 shows the diarrhea scores of Experiment Groups 2 and 3 and Comparative Group 2.

The results are shown in FIG. 4. FIG. 4 shows the diarrhea scores of Experiment Groups 2 and 3, and Comparative Group 2. Evaluation by scoring was made in a similar manner to Test Example 1. As shown in FIG. 4, recovery from diarrhea was very fast in the group that was given the substance containing proteins and insoluble dietary fibers. The degree was significantly better than from salazosulfapyridine, a drug currently used as a therapeutic drug for ulcerative colitis. The present experiment has shown that the administration of the substance containing proteins and insoluble dietary fibers can effectively promote amelioration of symptoms even if it is taken after development of ulcerative colitis. Similar results are confirmed for the substance containing proteins and insoluble dietary fibers according to Formulation Examples 2 through 4.

TEST EXAMPLE 3

The substance containing proteins and insoluble dietary. fibers prepared in Formulation Example 5 was tested to determine whether it could treat severe diarrhea associated with ulcerative colitis or abnormalities in the mucosa of colon.

Materials and Methods

These were basically the same as in Test Example 1. The feeds used in Test example 3 were as shown in Table 7. After breeding for 5 days, the appearances of the stool and the anus were examined and the appearance of diarrhea was evaluated by scoring.

Table 7 Table of Feed Composition

The method of preparing the basic feed was the same as in Test Example 1.

Test Example Group 3

The basic feed was supplemented with casein and cellulose to provide the protein and dietary fiber contents that would be given by adding 10% of the substance containing proteins and insoluble dietary fibers according to Formulation Example 5. Then, dextran sodium sulfate was added thereto at 4% to induce ulcerative colitis.

Experiment Group 4

The substance containing proteins and insoluble dietary fibers of Formulation Example 5 was added to the basic feed at 10%, and dextran sulfate sodium was added at 4% to induce ulcerative colitis.

|  | Comparative Group 3 | Experiment Group 4 |
|---|---|---|
|  | (% by weight) | |
| Casein | 14.6 | 10 |
| Mineral mix*1 | 3.5 | 3.5 |
| Vitamin mix*2 | 1 | 1 |
| Starch | 68.7 | 66.3 |
| Corn oil | 5 | 5 |
| Cellulose | 3 |  |
| The substance containing proteins and insoluble dietary fibers according to Formulation example 5 |  | 10 |
| Dextran sodium sulfate | 4 | 4 |
| Choline chloride | 0.2 | 0.2 |

*1 in conformity with AIN-93
*2 in conformity with AIN-93

Results

Figure 5:
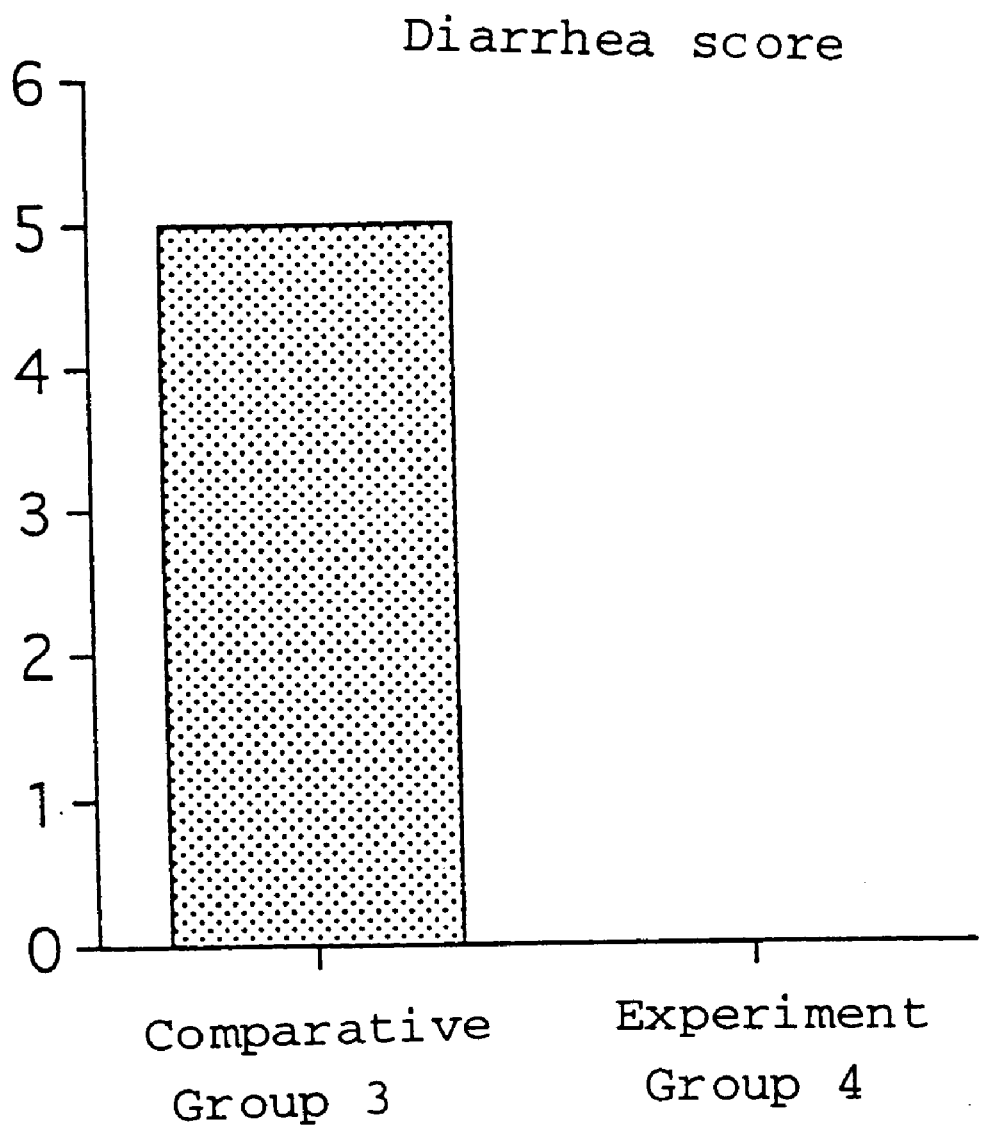
FIG. 5 shows the diarrhea scores of Experiment Group 4 and Comparative Group 3.

The results are shown in FIG. 5. FIG. 5 shows the diarrhea scores of Experiment Group 4, and Comparative Group 3. Evaluation by scoring was made in a similar manner to Test example 1. As shown in FIG. 5, the substance containing proteins and insoluble dietary fibers of Formulation Example 5 has also shown a very marked amelioration of main symptoms of ulcerative colitis.

TEST EXAMPLE 4

The substance containing proteins and insoluble dietary fibers prepared in Formulation Example 6 was tested to determine whether it could treat severe diarrhea associated with ulcerative colitis or abnormalities in the mucosa of colon.

Materials and Methods

As the test animal, male Std-ddY mice (6-week old, about 30 g) that had been acclimated to the experimental condition by a preparatory breeding with the solid feed (CE-2, Nippon clea) for one week were used in groups of five animals each. The feeds used in Test Example 4 were as shown in Table 8.

Ulcerative colitis was experimentally developed by giving the animal the feed mixed with dextran sodium sulfate. This is a modification of Iwanaga's method (Journal of Gastroenterology 29: 430–438, 1994). The substance containing proteins and insoluble dietary fibers was also given ad libitum in a mixture with the feed. After breeding for 3 days, the appearances of the stool and the anus were examined on day 4 and the state of diarrhea was evaluated by scoring.

Table 8 Composition of the Feed

The method of preparing the basic feed was the same as in Test Example 1.

Comparative Group 4

Dextran sodium sulfate was added to the basic feed at 4% to induce ulcerative colitis.

Experiment Group 5

After the substance containing proteins and insoluble dietary fibers according to Formulation Example 6 was added to the basic feed at 5%, dextran sodium sulfate was added at 4% to induce ulcerative colitis.

|  | Comparative Group 1 | Experiment Group 1 |
|---|---|---|
|  | (% by weight) | |
| Casein | 10 | 10 |
| Mineral mix*1 | 3.5 | 3.5 |
| Vitamin mix*2 | 1 | 1 |
| Starch | 73.3 | 71.3 |
| Corn oil | 5 | 5 |
| Cellulose | 3 |  |
| The substance containing proteins and insoluble dietary fibers according to Formulation Example 6 |  | 5 |
| Dextran sodium sulfate | 4 | 4 |
| Choline chloride | 0.2 | 0.2 |

*1 in conformity with AIN-93
*2 in conformity with AIN-93

Results

Figure 6:
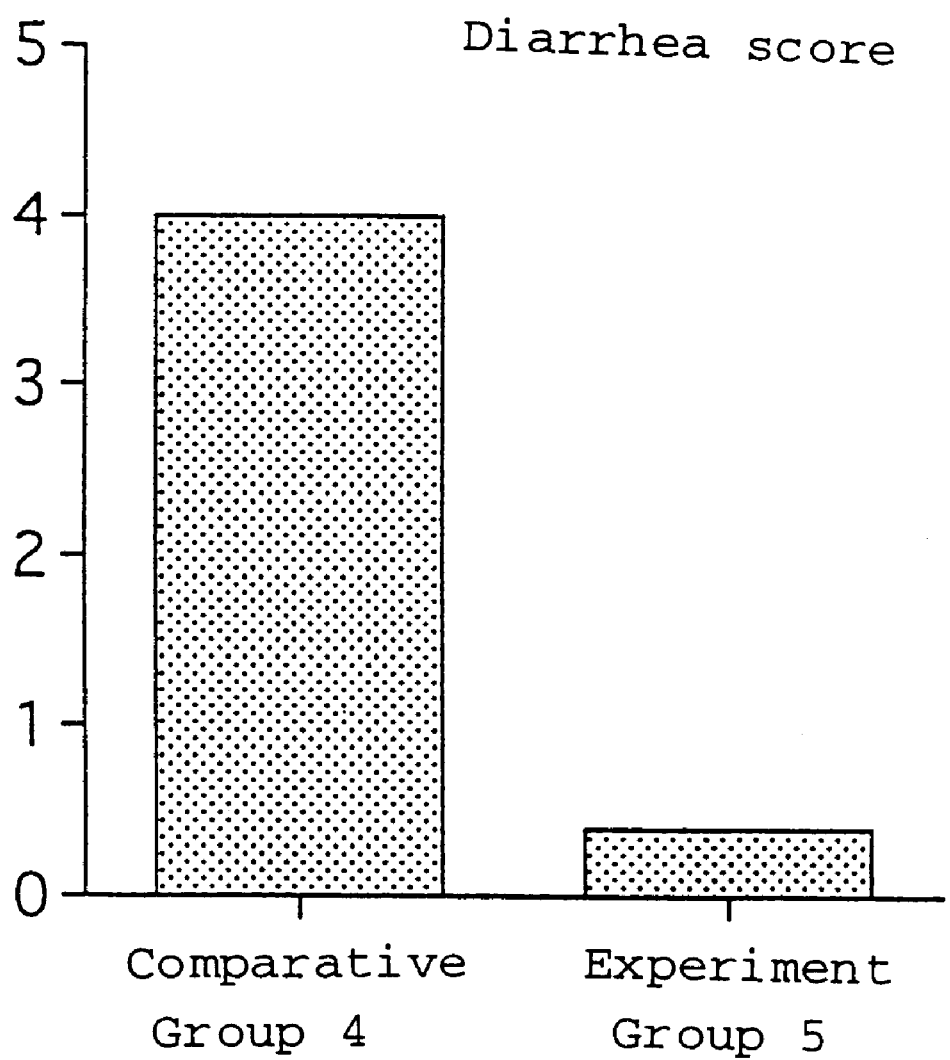
FIG. 6 shows the diarrhea scores of Experiment Group 5 and Comparative Group 4.

The results are shown in FIG. 6. FIG. 6 shows the diarrhea scores of Experiment Group 5 and Comparative Group 4. Evaluation by scoring was made in a similar manner to Test Example 1. As shown in FIG. 6, the substance containing proteins and insoluble dietary fibers according to Formulation Example 6 has also shown a very effective amelioration of main symptoms of ulcerative colitis.

TEST EXAMPLE 5

The substance containing proteins and insoluble dietary fibers prepared in Formulation Example 1 was tested to determine whether it could prevent or ameliorate severe damages on the mucosa of colon and diarrhea when anticancer agents were being used.

Materials and Methods

Male SD rats (4-week old), after preparatory breeding with the solid feed (CE-2, Nippon clea) for one week, were divided into groups of five animals each (body weight at the time of grouping was 136.2 g). They were then bred for one week by giving ad libitum the feed shown in Table 9. On day 7, 8 and 9, methotrexate (manufactured by Nippon Lederle) was given intraperitoneally at 5 mg/kg body weight. The animals were further bred for 5 days, and on day 5, after fasting for 4 hours, the jejunum (portions at 15 to 30 cm from the pylorus) was taken out under anesthesia with urethane. It was then fixed in formalin and embedded with paraffin and stained with hematoxylin-eosin for microscopic observation.

The following comparative examples were set up: 1) a comparative control group (cellulose was used as a dietary fiber) and 2) a group to which glutamin commonly held as an ideal nutrient for intestinal mucosa was added. On the last three days, stools were collected and their dry weight was measured.

Table 9 Table of Feed Composition

The method of preparing the basic feed was the same as in Test Example 1.

Comparative Group 1a

The basic feed was supplemented with casein and cellulose to provide the protein and dietary fiber contents that would be given by adding 10% of the substance containing proteins and insoluble dietary fibers according to Formulation Example 1.

Experiment Group 1a

The substance containing proteins and insoluble dietary fibers according to Formulation Example 1 was added to the basic feed at 10%.

Experiment Group 2a

Glutamin was added to the basic feed at 1.13%. This is equivalent to the content of glutamin obtained when the substance containing proteins and insoluble dietary fibers was added to the feed at 10%. Furthermore, casein and cellulose were added so that the weights of proteins and dietary fibers would be the same as in Experiment Group 1a.

|  | Comparative Group 1a | Experiment Group 1a (% by weight) | Experiment Group 2a |
|---|---|---|---|
| Casein | 14.6 | 10 | 13.47 |
| Mineral mix*1 | 3.5 | 3.5 | 3.5 |
| Vitamin mix*2 | 1 | 1 | 1 |
| Starch | 72.7 | 70.3 | 72.7 |
| Corn oil | 5 | 5 | 5 |
| Cellulose | 3 |  | 3 |
| The substance containing proteins and insoluble dietary fibers according to Formulation Example 1 |  | 10 |  |
| Glutamin |  |  | 1.13 |
| Choline chloride | 0.2 | 0.2 | 0.2 |

*1in conformity with AIN-93
*2in conformity with AIN-93

Results

Figure 8:
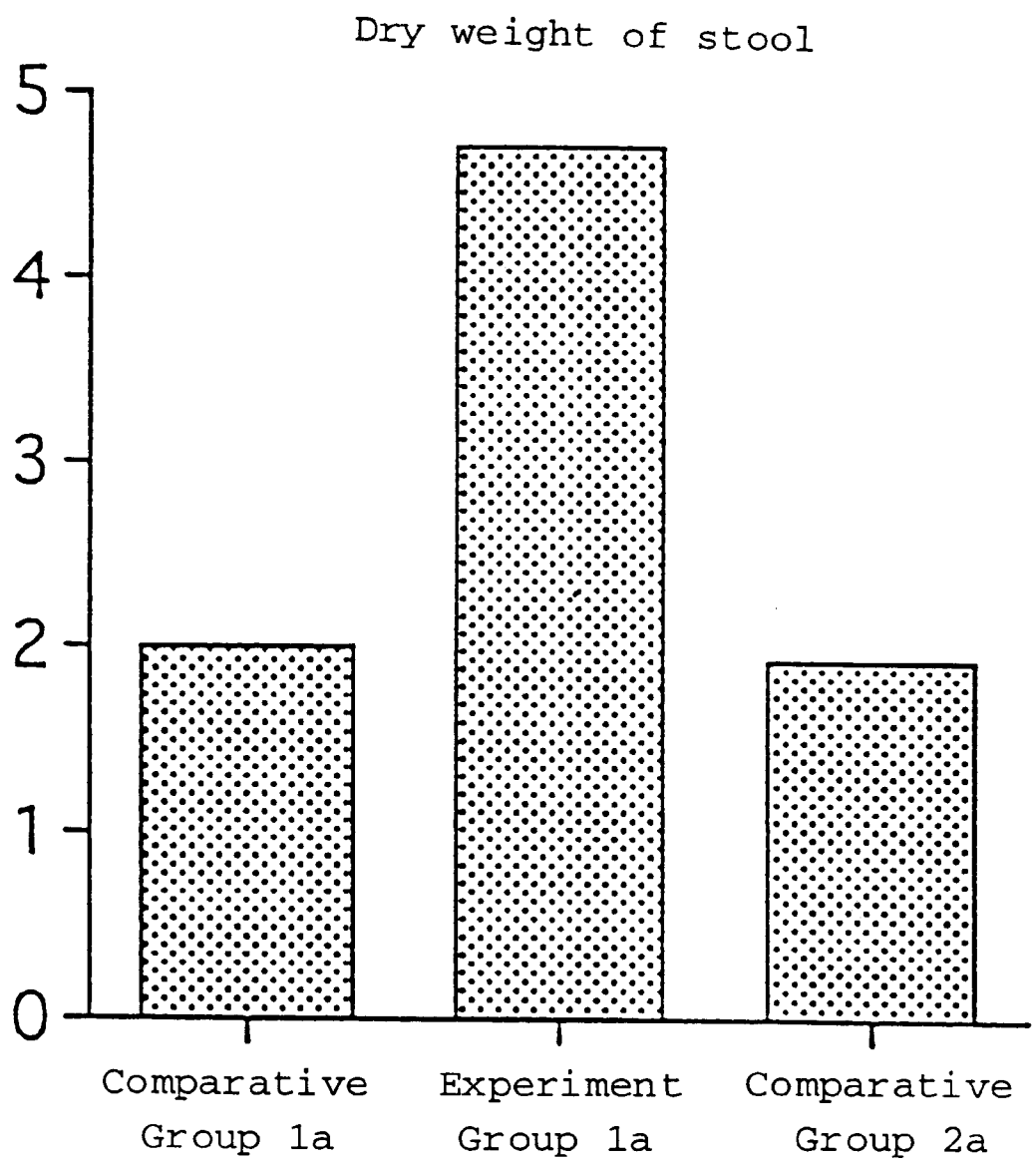

The results are shown in FIGS. 8 and 9. FIG. 8 shows the dry weight of the stools from Experiment Group 1a and Comparative Group 1a and 2a. Comparative Groups 1a and 2a had severe diarrhea. FIG. 9 shows the appearance of the mucosas of the small intestines of Experiment Group 1a and Comparative Groups 1a and 2a (9-2, 9-1, and 9-3, respectively) As shown in FIGS. 8 and 9, excretion of the stool was normal in Experiment Group 1a that took the substance containing proteins and insoluble dietary fibers, but a reduction in the dry weight of stool excretion was observed in Comparative Groups 1a and 2a due to diarrhea. In the examination of the mucosa of the intestine, images of normal mucosa were observed only when the substance containing proteins and insoluble dietary fibers was taken and this suggests that the substance protects the intestinal mucosa from side effects of the anti-cancer agent.

TEST EXAMPLE 6

The substance containing proteins and insoluble dietary fibers prepared in Formulation Example 1 was tested to determine whether it could reduce or prevent the damage that would otherwise be caused on the intestinal mucosa by radiation exposure.

Materials and Methods

Male ST-Wistar rats (3-week old), after preparatory breeding with the casein-sucrose diet (the basic feed or Comparative Group 3a as shown in Table 10) for one week, were divided into groups of seven animals each. Subsequently, the animals were fed the test feed shown in Table 10 for 10 days, and on day 11 they were exposed to a radiation of 10 Gy (from 60Co) in a localized area (lower abdomen). They were bred for 8 more days and the effect of the substance containing proteins and insoluble dietary fibers to prevent the damage on the intestinal mucosa due to radiation exposure was evaluated in terms of the survival rate.

Table 10 Table of Feed Composition

Comparative Group 3a

The sucrose basic feed group with 20% casein and 0% dietary fiber

Experiment Group 2a

The substance containing proteins and insoluble dietary fibers prepared in Formulation example 1 was added to the sucrose basic feed at 10% and its sucrose content was accordingly reduced.

|  | Comparative Group 3a | Experiment Group 2a |
|---|---|---|
|  | (% by weight) | |
| Casein | 20 | 20 |
| Mineral mix | 3.5 | 3.5 |
| Vitamin mix | 1 | 1 |
| Starch | 70.3 | 60.3 |
| Corn oil | 5 | 5 |
| The substance containing proteins and insoluble dietary fibers according to Formulation example 1 |  | 10 |
| Choline chloride | 0.2 | 0.2 |

Results

As shown in Table 11, a reduction in mortality was observed only when the substance containing proteins and insoluble dietary fibers was taken by the test animals. This is believed to result from the reduction in the radiation damage on the intestinal mucosa.

TABLE 11

Survival rate on day 8 of radiation exposure

|  | Comparative Group 3a | Experiment Group 2a |
|---|---|---|
| (No. of viable animals/total No. tested) | (5/7) | (7/7) |

TEST EXAMPLE 7

The substance containing proteins and insoluble dietary fibers prepared in Formulation example 1 was tested to determine whether it would permit normal stool formation when a massive ablation of the lower gastrointestinal tract (the large intestine) was carried out.

Materials and Methods

As the test animal, male SD rats (4-week old, about 50 g) that had been acclimated to the experimental condition by a preparatory breeding with the feed shown in Table 12 for one week were used in groups of 10 animals each. The large intestine was removed in such a way that the anus and the large intestine within the pelvis were left intact; then, an end-to-end anastomosis of the small intestine was conducted. After a recovery period of 2 days, the animals were given again the feed shown in Table 12 and bred for one week, and the appearance of the stool and the anus were examined.

Table 12 Table of Feed Composition

The method of preparing the basic feed was the same as in Test Example 1.

Comparative Group 1b

The basic feed was supplemented with casein and cellulose to provide the protein and dietary fiber contents that would be given by adding 10% of the substance containing proteins and insoluble dietary fibers according to Formulation Example 1.

Experiment Group 1b

The substance containing proteins and insoluble dietary fibers according to Formulation Example 1 was added to the basic feed at 10%.

|  | Comparative Group 1b | Experiment Group 1b |
|---|---|---|
|  | (% by weight) | |
| Casein | 14.6 | 10 |
| Mineral mix*[1] | 3.5 | 3.5 |
| Vitamin mix*[2] | 1 | 1 |
| Starch | 72.7 | 70.3 |
| Corn oil | 5 | 5 |
| Cellulose | 3 | |
| The substance containing proteins and insoluble dietary fibers according to Formulation Example 1 | | 10 |
| Choline chloride | 0.2 | 0.2 |

*[1]in conformity with AIN-93
*[2]in conformity with AIN-93

Results

Figure 10:
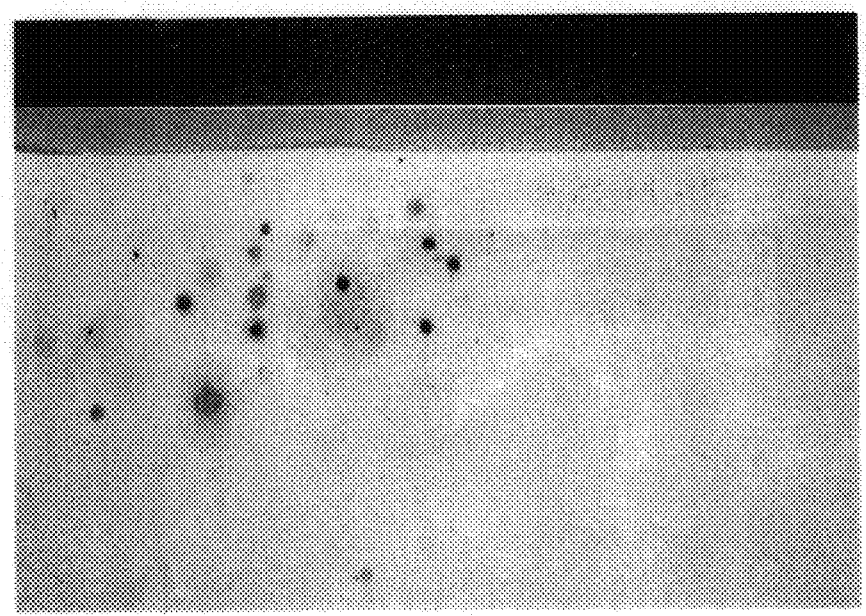
FIG. 10 is a pair of photographs showing the appearance of stools from Experiment Group 1b and Comparative Group 1b.
Figure 10:
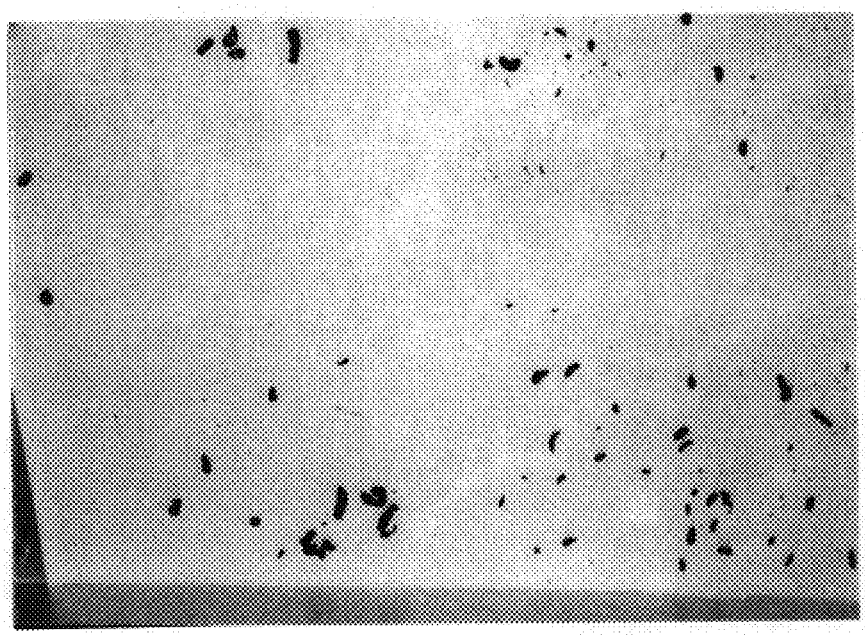
Figure 11:
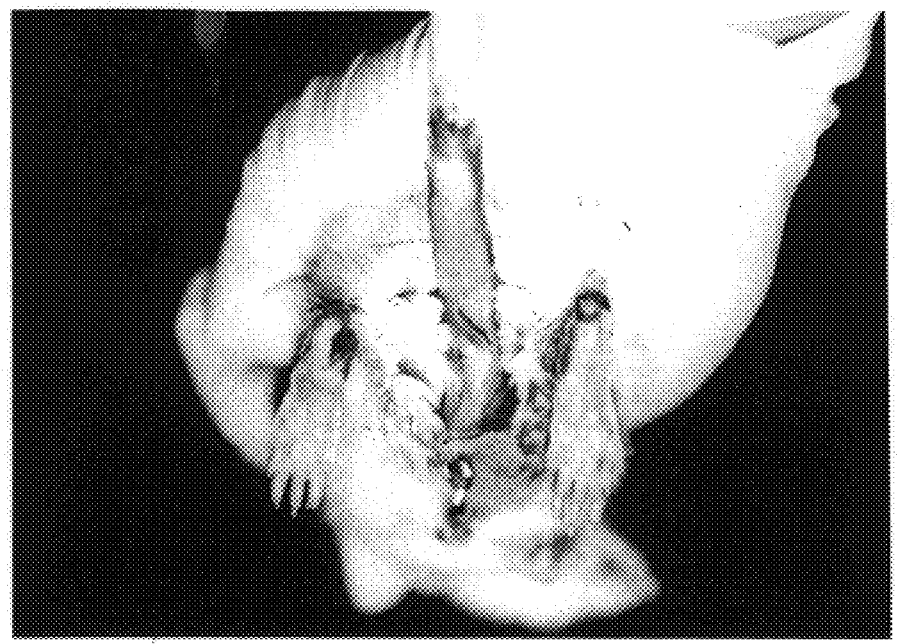
FIG. 11 is a pair of photographs showing the peripheral appearance of the anuses of Experiment Group 1b and Comparative Group 1b.
Figure 11:
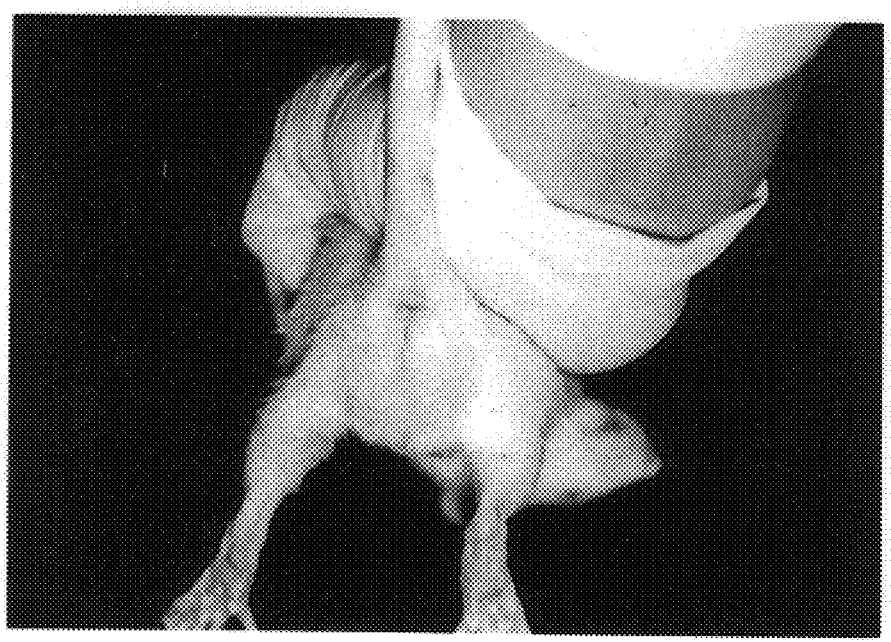

Examination of the stool and the anus was conducted on the last day of breeding and the results are shown in FIGS. 10 and 11: fairly severe diarrhea with liquid stools was noted in Comparative Group 1b whereas the stool had an almost normal appearance in Experiment Group 1b.

Examination of the periphery of the anus revealed that severe erosion due to diarrhea was noted in Comparative Group 1b whereas no erosion was observed to give an almost normal appearance in Experiment Group 1b because of the component of interest in Formulation Example 1.

The substance containing proteins and insoluble dietary fibers permitted normal stool formation very effectively after ablation of the gastrointestinal tract.

FORMULATION EXAMPLE 7

After accurate weight measurement, dry barley malt was scraped from the husk surface with TDB2A, a rice whiting machine for brewery use (manufactured by Satake Seisakusho; working rotational speed, 500 rpm). The scraped malt grains which weighed 88–80% of the initial barley malt were obtained as the substance containing proteins and insoluble dietary fibers. Its protein and dietary fiber contents were 11.5% and 30%, respectively.

For comparison, ungerminated barley was fractionated under the same conditions as described above. The resulting substance containing proteins and insoluble dietary fibers had protein and dietary fiber contents of 16.3% and 31.5%, respectively.

FORMULATION EXAMPLE 8

Germinated rice was dried and dehusked. After accurate weight measurement, the dehusked grains were scraped from the surface with TDB2A, a rice whiting machine for brewery use (manufactured by Satake Seisakusho; working rotational speed, 500 rpm). The scraped rice grains which weighed 100–95% of the initial rice grains were obtained as the substance containing proteins and insoluble dietary fibers. Its protein and dietary fiber contents were 17.6% and 21.6%, respectively.

For comparison, ungerminated brown (dehusked) rice was fractionated under the same conditions as described above. The resulting substance containing proteins and insoluble dietary fibers had protein and dietary fiber contents of 16.3% and 28.5%, respectively.

TEST EXAMPLE 8

The effect of the substance containing proteins and insoluble dietary fibers prepared in Test Examples 7 and 8 was investigated.

Materials and Methods

The same as in Test Example 1. The feeds used in Test Example 8 were as shown in Table 13.

Table 13 Table of Feed Composition

The method of preparing the basic feed was the same as in Test Example 1.

Comparative Group 5

Same as the feed for Experiment Group 6, except that no substance containing proteins and insoluble dietary fibers was added and that it was supplemented with casein and cellulose to provide the corresponding protein and dietary fiber contents. It contained 3.5% of dextran sodium sulfate in order to induce ulcerative colitis.

Comparative Group 6

The substance containing proteins and insoluble dietary fibers which was derived from "ungerminated barley" and prepared in Formulation Example 7 was added to the basic feed at 10%, and dextran sodium sulfate was added at 3.5% in order to induce ulcerative colitis.

Experiment Group 6

The substance containing proteins and insoluble dietary fibers which was derived from barley malt and prepared in Formulation Example 7 was added to the basic feed at 10%, and dextran sodium sulfate was added at 3.5% in order to induce ulcerative colitis.

Comparative Group 7

The substance containing proteins and insoluble dietary fibers which was derived from "ungerminated brown rice" and prepared in Formulation Example 8 was added to the basic feed at 10%, and dextran sodium sulfate was added at 3.5% in order to induce ulcerative colitis.

Experiment Group 7

The substance containing proteins and insoluble dietary fibers which was derived from germinated rice grains and prepared in Formulation Example 8 was added to the basic feed at 10%, and dextran sodium sulfate was added at 3.5% in order to induce ulcerative colitis.

|  | Comp. Group 5 | Comp. Group 6 | Exp. Group 6 | Comp. Group 7 | Exp. Group 7 |
|---|---|---|---|---|---|
|  | (% by weight) | | | | |
| Casein | 14.6 | 13.0 | 13.3 | 13.0 | 12.8 |
| Mineral mix | 1 | 1 | 1 | 1 | 1 |
| Vitamin mix | 3.5 | 3.5 | 3.5 | 3.5 | 3.5 |
| Starch | 69.4 | 64.0 | 63.55 | 63.85 | 63.36 |
| Cellulose | 3 | 0.15 | 0.15 | 0.84 | |
| Corn oil | 5 | 5 | 5 | 5 | 5 |
| The substance containing proteins and insoluble dietary fibers derived from ungerminated barley according to Formulation Example 7 | | 10 | | | |
| The substance containing proteins and insoluble dietary fibers derived from barley according to Formulation Example 7 | | | 10 | | |
| The substance containing proteins and insoluble dietary fibers derived from ungerminated brown rice according to Formulation Example 8 | | | | 10 | |
| The substance containing proteins and insoluble dietary fibers derived from germinated rice according to Formulation Example 8 | | | | | 10 |
| Dextran sodium sulfate | 3.5 | 3.5 | 3.5 | 3.5 | 3.5 |

Results

Figure 7:
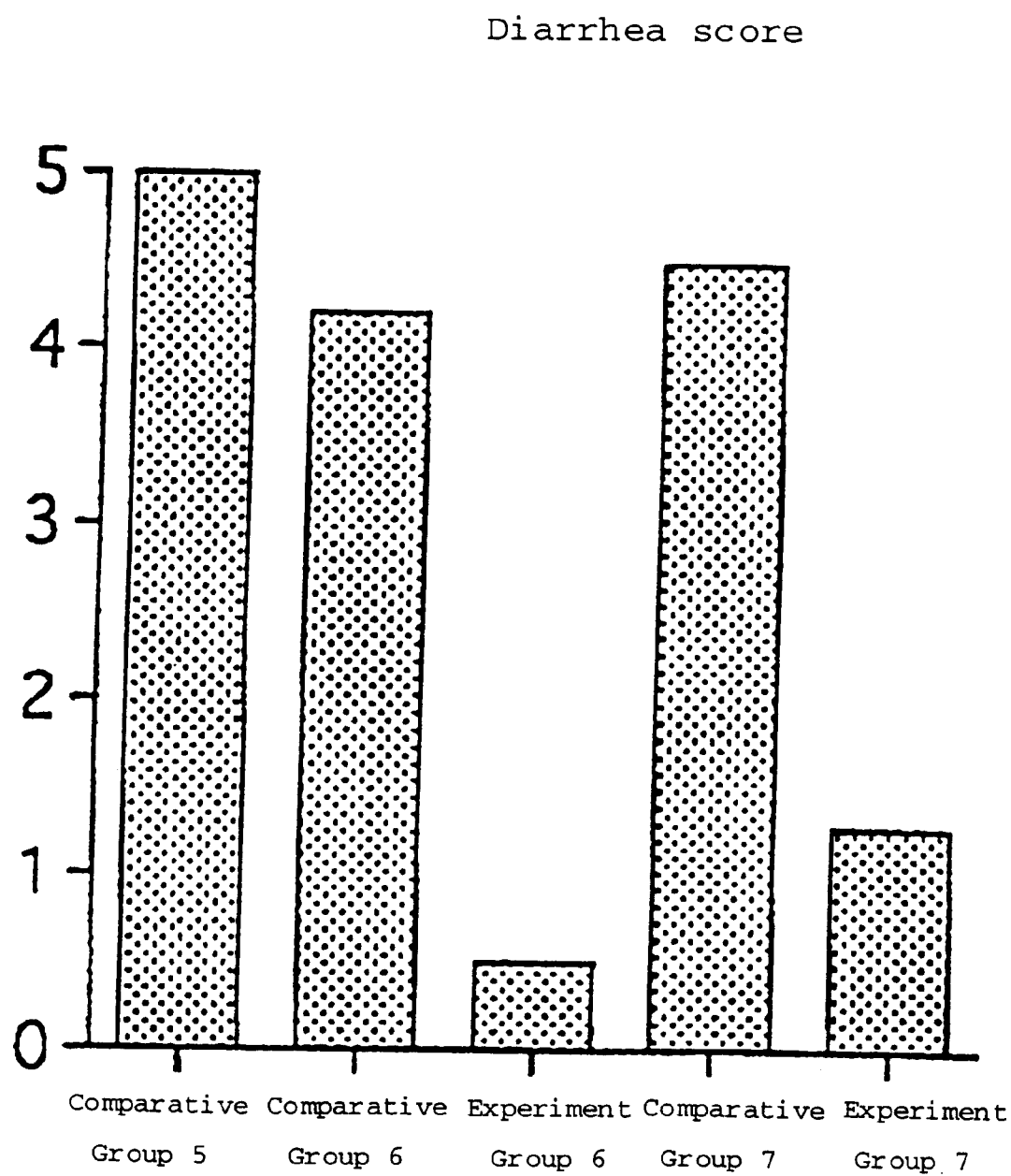
FIG. 7 shows the diarrhea scores of Experiment Groups 6 and 7 and Comparative Groups 5 through 7.

The results of the investigation on Experiment Groups 6 and 7, and Comparative Groups 5 through 7 described in Table 13 are shown in FIG. 7. The diarrhea scores in FIG. 7 were evaluated in the same manner as in Test Example 1.

As shown in FIG. 7, the diarrhea score decreased only when the substances containing proteins and insoluble dietary fibers that derived from the germinated barley and the germinated rice was taken by the animals. Therefore, it was demonstrated that both of these substances containing proteins and insoluble dietary fibers can prevent the severe diarrhea associated with ulcerative colitis.

In Test Example 8, none of the experiment groups showed measurable changes in body weight.

FORMULATION EXAMPLE 9

After accurate weight measurement, dried and dehusked rye malt was scraped from the grain surface with TDB2A, a rice whiting machine for brewery (manufactured by Satake Seisakusho; working rotational speed, 500 rpm).

The scraped rye malt grains which weighed 100–96% of the initial rye malt grains were obtained as the substance containing proteins and insoluble dietary fibers. Its protein and dietary fiber contents were 16.3% and 35%, respectively.

FORMULATION EXAMPLE 10

After accurate weigh measurement, dried and dehusked rye was scraped from the grain surface with TDB2A, a rice whiting machine for brewery use (manufactured by Satake Seisakusho; working rotational speed, 500 rpm). The scraped rye grains which weighed 100–96% of the initial rye grains were obtained as the substance containing proteins and insoluble dietary fibers. Its protein and dietary fiber contents were 12.9% and 35%, respectively.

The analytical values of these substances are as shown in Table 14.

TABLE 14

Table of ingredients

|  | Formulation Example 9 | Formulation Example 10 |
|---|---|---|
|  | (% by weight) | |
| Crude protein | 16.3 | 12.9 |
| Crude fat | 3.8 | 4.2 |
| Ash content | 2.6 | 3.7 |
| Dietary fiber | 35.0 | 35.0 |

TEST EXAMPLE 9

The substance containing proteins and insoluble dietary fibers prepared in Formulation Example 9 was tested to determine whether it could treat the severe diarrhea associated with ulcerative colitis or abnormalities in the mucosa of colon. The same test was conducted with the fractions obtained in Formulation Example 10.

Materials and Methods

As the test animal, male SD rats (3-week old, about 50 g) that had been acclimated to the experimental condition by a preparatory breeding with a solid feed for one week were used in groups of five animals each. The feeds used in Test Example 9 were as shown in Table 15.

The substances containing proteins and insoluble dietary fibers prepared in Formulation Examples 9 and 10 were also given ad libitum in admixture with the feed. After breeding for 5 days, the appearance of the stool and the anus was examined and the severity of diarrhea was evaluated by scoring. Then the colon was ablated totally and fixed in 10% formalin to prepare sections of the mucosa, and the images of the mucosa were also examined. The results were, as shown in Table 16; the amelioration of diarrhea and the prevention of erosion in the anus and damage on the mucosa of the large intestine were possible only when the substance containing proteins and insoluble dietary fibers prepared in Formulation Example 9 was taken by the animals.

The severity of diarrhea was classified into 6 levels: 0, normal; 1, slightly soft; 2, considerably soft; 3, stools could not be picked up; 4, diarrhea+slightly eroded anus; 5, diarrhea+badly eroded anus. Also, the damage on the mucosa of the large intestine was scored in accordance with the method of Morris, in which the larger number means a severer damage.
Table 15 Table of Feed Composition The method of preparing the basic feed was the same as in Test Example 1.
Comparative Group 1c The basic feed was supplemented with casein and cellulose to provide the protein and dietary fiber contents that would be given by adding 10% of the substance containing proteins and insoluble dietary fibers according to Formulation Example 1. Dextran sodium sulfate was added at 4% to induce ulcerative colitis.
Comparative Group 2c The substance containing proteins and insoluble dietary fibers according to Formulation Example 10 was added to the basic feed at 10%, and dextran sodium sulfate was added at 4% in order to induce ulcerative colitis. Casein and cellulose were also added to give the same protein and dietary fiber contents as in Comparative Group 1c.
Experiment Group 1c The substance containing proteins and insoluble dietary fibers according to Formulation Example 9 was added to the basic feed at 10%, and dextran sodium sulfate was added at 4% in order to induce ulcerative colitis. Casein and cellulose were also added to give the same protein and dietary fiber contents as in Comparative Group 1c.

|  | Comparative Group 1c | Experiment Group 2c | Experiment Group 1c |
|---|---|---|---|
|  | (% by weight) | | |
| Casein | 14.6 | 13.3 | 12.9 |
| Mineral mix*1 | 3.5 | 3.5 | 3.5 |
| Vitamin mix*2 | 1 | 1.0 | 1.0 |
| Starch | 68.7 | 63.0 | 63.4 |
| Corn oil | 5.0 | 5.0 | 5.0 |
| Cellulose | 3.0 | | |
| The substance containing proteins and insoluble dietary fibers according to Formulation Example 10 | | 10.0 | |
| The substance containing proteins and insoluble dietary fibers according to Formulation Example 9 | | | 10.0 |
| Dextran sodium sulfate | 4.0 | 4.0 | 4.0 |
| Choline chloride | 0.2 | 0.2 | 0.2 |

*1 in conformity with AIN-93
*2 in conformity with AIN-93

Results

The results of the above experiment were as shown in Table 16. The substance containing proteins and insoluble dietary fibers prepared in Test Example 9 was capable of treating the diarrhea peculiar to ulcerative colitis and it was also very effective in preventing the damage that would otherwise be caused on the mucosa of the large intestine.

TABLE 16

|  | Diarrhea score | Score of damage on the mucosa of the large intestine |
|---|---|---|
| Comparative Group 1c | 5.0 | 4.2 |
| Comparative Group 2c | 3.8 | 5.7 |
| Experiment Group 1c | 0.4 | 2.5 |

FORMULATION EXAMPLE 11

The method shown in Formulation Example 2 was repeated, except that a different kind of brewer's grains was used as the raw material and that the drying with dry heat (steam dryer) was replaced by lyophilization. Thus, the brewer's grains in the wet state were pressed and milled and then screened using a 50-mesh sieve within water. The fraction that passed through the sieve was subjected to preliminary freezing at −20° C. and then lyophilized according to the standard method.

The results of analysis are shown in Tables 17 and 18.

TABLE 17

Table of Ingredients

|  | (% by weight) |
|---|---|
| Crude protein | 50.2 |
| Crude fat | 13.7 |
| Ash content | 1.5 |
| Dietary fiber | 33.6 |

TABLE 18

Composition of Dietary fibers

|  | (%) |
|---|---|
| Hemicellulose | 69.9 |
| Cellulose | 23.3 |
| Lignin | 6.8 |

A test was conducted with the substance as shown below.

TEST EXAMPLE 10

The substance containing proteins and insoluble dietary fibers prepared in Formulation Example 11 was tested to determine whether it could treat the severe diarrhea associated with ulcerative colitis or abnormalities in the mucosa of the large intestine.

Materials and Methods

The test animals and the method of developing ulcerative colitis were as shown in Test Example 1, except that the feeds used in Test Example 10 were as shown in Table 19 below.

TABLE 19

|  | Comparative Example 1 | Experiment Example 1 |
|---|---|---|
|  | (% by weight) | |
| Casein | 14.6 | 10 |
| Mineral mix*1 | 3.5 | 3.5 |
| Vitamin mix*2 | 1.0 | 1.0 |
| Starch | 69.2 | 66.8 |
| Corn oil | 5.0 | |
| Cellulose | 3.0 | |
| The substance containing proteins and insoluble dietary fibers according to Formulation Example 11 | | 10.0 |
| Choline chloride | 0.2 | 0.2 |
| dextran sodium sulfate | 3.5 | 3.5 |

*1 in conformity with AIN-93
*2 in conformity with AIN-93

Results

The results are shown in Table 20. In Experiment Example 1 the diarrhea score decreased and no erosion was observed in the periphery of the anus.

TABLE 20

| Comparative Example 1 | 5.0 |
|---|---|
| Experiment Example 1 | 0.2 |

It will be readily recognized by a person skilled in the art that aside from the substances tested in the above Test Examples, those which are derived from the germinated seeds of plants of a grass family which are within the scope of the present invention would have similar effects.

INDUSTRIAL APPLICABILITY

The substance derived from the germinated seed of a grass family plant of the present invention is capable of treating the diarrhea associated with ulcerative colitis and it is also effective in preventing disorders of the mucosa of the large intestine. In addition, the substance derived from the germinated seed of a grass family plant of the present invention can effectively prevent damages on the intestinal mucosa and control the ensuing onset of diarrhea, both symptoms being severe side effects resulting from administration of anti-cancer agents. Furthermore, the substance derived from the germinated seed of a grass family plant of the present invention can effectively improve the bowel movement of a patient who has undergone intestinal ablation or a patient with an artificial anus. Moreover, the substance derived from the germinated seed of a grass family plant of the present invention has no side effects.

What is claimed is:

1. A method of avoiding or reducing damage to the intestinal mucosa and the resultant diarrhea, the method comprising administering to a patient with a cancer an effective amount of a substance which was isolated from the germinated seed of a barley, rice, or rye plant and which contains 10% to 70% protein by weight and 20 to 70% insoluble dietary fiber by weight.

2. A method of prophylactic or therapeutic treatment of damage to the intestinal mucosa and the resultant diarrhea, comprising administering at least one gram of a substance isolated from fractions containing the aleurone layer and the germ of the germinated seed of a brewer's grain, said substance comprising 10% to 70% protein by weight and 20 to 70% insoluble dietary fiber by weight.

3. A substance isolated from the germinated seed of a barley, rice, or rye plant which comprises 10 to 70% protein by weight and 20 to 70% insoluble dietary fiber by weight and wherein the isolated substance is obtained by passing through a sieve of 50 mesh.

4. The substance of claim 3, wherein the substance comprises the aleurone layer and the germ of the germinated seed.

5. A substance isolated from the germinated seed of a barley, rice, or rye plant which comprises 10 to 70% protein by weight and 20 to 70% insoluble dietary fiber by weight, wherein the isolated substance is obtained by passing through a sieve of 50 mesh and the protein has been converted by enzyme treatment to smaller molecules having an average length of about 5 to 8 amino acids.

6. The substance of claim 5, wherein the substance comprises the aleurone layer and the germ of the germinated seed.

7. A substance isolated from the germinated seed of a barley, rice, or rye plant which comprises 10 to 70% protein by weight and 20 to 70% insoluble dietary fiber by weight, wherein the isolated substance is obtained by passing through a sieve of 50 mesh and the concentration of insoluble dietary fibers, relative to the concentration of protein, has been increased by enzyme treatment and filtration.

8. The substance of claim 7, wherein the substance comprises the aleurone layer and the germ of the germinated seed.

9. A method for preventing or reducing damage to the intestinal mucosa comprising administering to a patient in need thereof an effective amount of a substance isolated from the germinated seed of a barley, rice, or rye plant, wherein the substance comprises 10 to 70% protein by weight and 20 to 70% insoluble dietary fiber by weight.

10. The method of claim 9, wherein the substance comprises the aleurone layer and the germ of the germinated seed.

11. The method of claim 9, wherein the proteins have been converted by enzyme treatment to smaller molecules having an average length of about 5 to 8 amino acids.

12. The method of claim 9, wherein the concentration of insoluble dietary fibers, relative to the concentration of protein, has been increased by enzyme treatment and filtration.

13. The method of claim 9, wherein the damage to the intestinal mucosa causes diarrhea.

14. The method of claim 9, wherein the damage to the intestinal mucosa is caused by a cancer treatment.

15. A method for treating diarrhea, wherein the diarrhea is caused by damage to the intestinal mucosa, comprising administering to a patient in need thereof an effective amount of a substance isolated from the germinated seed of a barley, rice, or rye plant, wherein the substance comprises 10 to 70% protein by weight and 20 to 70% insoluble dietary fiber by weight.

16. The method of claim 15, wherein the substance comprises the aleurone layer and the germ of the germinated seed.

17. The method of claim 15, wherein the proteins have been converted by enzyme treatment to smaller molecules having an average length of about 5 to 8 amino acids.

18. The method of claim 15, wherein the concentration of insoluble dietary fibers, relative to the concentration of protein, has been increased by enzyme treatment and filtration.

19. The method of claim 15, wherein the damage to the intestinal mucosa is caused by a cancer treatment.

* * * * *

UNITED STATES PATENT AND TRADEMARK OFFICE
CERTIFICATE OF CORRECTION

PATENT NO.    : 6,348,221 B1
DATED         : February 19, 2002
INVENTOR(S)   : Osamu Kanauchi et al.

It is certified that error appears in the above-identified patent and that said Letters Patent is hereby corrected as shown below:

<u>Title page,</u>
Item [*], Notice: "Subject to any disclaimer, the term of this patent is extended or adjusted under 35 U.S.C. 154 (b) by 0 days" should read -- Subject to any disclaimer, the term of this patent is extended or adjusted under 35 U.S.C. 154(b) by 10 days --.

Signed and Sealed this

Twenty-fourth Day of September, 2002

*Attest:*

*Attesting Officer*

JAMES E. ROGAN
*Director of the United States Patent and Trademark Office*